United States Patent [19]

Crawford

[11] 4,229,364
[45] Oct. 21, 1980

[54] SYNTHESIS OF 1,4-BIS(DICYANOMETHYLENE) CYCLOHEXANE

[75] Inventor: Robert J. Crawford, Cincinnati, Ohio

[73] Assignee: The Procter & Gamble Company, Cincinnati, Ohio

[21] Appl. No.: 38,594

[22] Filed: May 14, 1979

[51] Int. Cl.$^3$ .................. C07C 120/00; C07C 121/48
[52] U.S. Cl. ............................... 260/464; 260/396 N
[58] Field of Search ........................... 260/464, 396 N

[56] References Cited

U.S. PATENT DOCUMENTS

| 2,675,390 | 4/1954 | Rosenblatt | 568/833 X |
| 3,115,506 | 12/1963 | Acker et al. | 260/464 X |

OTHER PUBLICATIONS

Perlstein, Angew. Chem. Int. Ed. Engl., 16, (1977), pp. 519–534.
Soos, J. Chem. Education, 55, (1978), pp. 546–552.
Acker, et al., J.A.C.S., 84, (1962), pp. 3370–3374.
Adkins, et al., J.A.C.S., 70, (1948), pp. 695–698.
Owen, et al., J. Chem. Soc., (1949), pp. 320–326.
Olberg, et al., J.A.C.S., 66, (1944), pp. 1096–1099.
Dimroth, Ber., 72B, (1939), pp. 2043–2051.
Sircar, et al., J. Org. Chem., 30, (1965), pp. 3206–3207.
Morita, C.A., 85, (1976), 32525-w.
Fatiadi, Synthesis, (1978), pp. 241–243, 178.
Nielsen, et al., Org. Syn. Coll., vol. V, pp. 288–291.
C. A., 81, 151638n, 1974, Lyubomilov et al.
C. A., 72, 132156b, 1970, Iijima et al.
C. A., 73, 124007i, 1970, Taira et al.
C. A., 55, 7349, 1961, Kern et al.
C. A., 54, 5552, 1960, Izumi.
C. A., 55, 19821, 1961, Lichtenberger et al.
C. A., 44, 3445, 1950, Fujita.
C. A., 36, pp. 2838–2839, 1942, Palfray.
Gogek, et al., Can. Jour. of Chem., 29, pp. 946–948, 1951.
Wolfe, et al., Chem. Communications, pp. 1420–1421, 1970.
Mussini, et al., Synthetic Communications, 5, pp. 283–286, 1975.
C. A., 85, 32525w, 1976, Morita.
C. A., 41, 4111, 1947, Vene.

Primary Examiner—Joseph Paul Brust
Attorney, Agent, or Firm—Richard C. Witte; Jerry J. Yetter; Jack D. Schaeffer

[57] ABSTRACT 1,4-Bis(dicyanomethylene)cyclohexane is the chemical of choice for the synthesis of TCNQ. The present invention provides a simple convenient, three-step synthesis of 1,4-bis(dicyanomethylene)cyclohexane from hydroquinone which uses water as the reaction solvent.

6 Claims, No Drawings

SYNTHESIS OF 1,4-BIS(DICYANOMETHYLENE) CYCLOHEXANE

TECHNICAL FIELD

The present invention encompasses a chemical process for preparing a precursor of TCNQ.

7,7,8,8-Tetracyanoquinodimethane (TCNQ) is a unique organic molecule because of its ability to accept electrons from donor substances. It is one of the most powerful electron acceptors known. This property has stimulated extensive research interest during the last decade. For example, TCNQ cn be combined with strong electron donors to form crystalline complexes which have electrical conductivities approaching those of metals, and many workers are now investigating TCNQ complexes in order to develop organic metals and organic semiconductors.

TCNQ is also used as the essential catalytic ingredient in the fatty acid alpha-chlorination process disclosed in U.S. Pat. No. 4,148,811, Crawford, issued Apr. 10, 1978.

All practical chemical syntheses of TCNQ require the use of 1,4-bis(dicyanomethylene)cyclohexane as the immediate precursor to TCNQ. This cyclohexane derivative is converted to TCNQ by various known methods.

The present invention provides an extremely simple and convenient process for the synthesis of 1,4-bis(-dicyanomethylene)cyclohexane from a readily available commercial chemical, hydroquinone. The process is designed in such a way that it is readily adaptable to large scale commercial use. In particular, the process uses water as the only solvent throughout the three synthetic steps, and unexpectedly high yields are secured. Since 1,4-bis(dicyanomethylene)cyclohexane is the essential precursor to TCNQ, the development constitutes a practical synthesis of TCNQ, itself.

BACKGROUND ART

The following publications relate to the synthesis of TCNQ and to various synthetic steps relevant to the practice of the present invention. The publications, which are referenced by number throughout the specification, are incorporated herein by reference.

1. J. H. Perlstein, *Angew. Chem. Int. Ed. Engl.*, 16, 519 (1977).
2. Z. G. Soos, *J. Chem. Education*, 55, 546 (1978).
3. A. J. Fatiadi, *Synthesis*, 241 (1978).
4. D. S. Acker and W. R. Hertler, *J. Am. Chem. Soc.*, 84, 3370 (1962).
5. A. T. Nielsen and W. R. Carpenter, *Org. Syn. Coll.* Vol. V, p. 288.
6. H. Adkins and H. R. Billica, *J. Am. Chem. Soc.*, 70, 695 (1948).
7. U.S.S.R. Patent 436,044; *Chem. Abstr.*, 81, 151638 (1974).
8. Japanese Patent 7006009; *Chem. Abstr.*, 72, 132156 (1970).
9. Japanese Patent 7016097; *Chem. Abstr.*, 73 124007 (1970).
10. W. Kern, W. Gruber, and H. O. Wirth, *Makromol. Chem.*, 37, 198 (1960); Chem. Abstr., 55, 7349 (1961).
11. I. Motoyama, *Nippon Kagaku Zasshi*, 79, 1296 (1958); *Chem. Abstr.*, 54, 5552 (1960).
12. J. Lichtenberger and J. Hincky, *Bull. Soc. Chim. France*, 354 (1961); *Chem. Abstr.*, 55, 19821 (1961).
13. S. Fujita, *Mem. Coll. Sci. Kyoto Imp. Univ.*, 23A, 405 (1942); *Chem. Abstr.*, 44, 3445 (1950).
14. L. N. Owen and P. A. Robins, *J. Chem. Soc.*, 320 (1949); *Chem. Abstr.*, 43, 7435 (1949).
15. R. C. Olberg, H. Pines, and V. N. Ipatieff, *J. Am. Chem. Soc.*, 66, 1096 (1944); *Chem. Abstr.*, 38, 4913 (1944).
16. K. Dimroth, *Chem. Ber.*, 72B, 2043 (1939); *Chem. Abstr.*, 34, 3242 (1940).
17. L. Palfray, *Bull. Soc. Chim. France*, 7, 407, (1940); *Chem. Abstr.*, 36, 2838 (1942).
18. C. J. Gogek, R. Y Moir, and C. B. Purves, *Can. J. Chem.*, 29, 946 (1951).
19. J. C. Sircar and A. I. Meyers, *J. Org. Chem.*, 30, 3206 (1965).
20. S. Wolfe, S, K, Hasan, and J. R. Campbell, *Chem. Communications*, 1420 (1970).
21. P. Mussini, F. Orsini, and F. Pelizzoni, *Synthetic Communications*, 5, 283 (1975).
22. Japanese Patent 7616643; *Chem, Abstr.*, 85, 32525 (1976).
23. J. Vene, *Bull. Soc. Sci. Bretagne*, 20, 11 (1945); *Chem, Abstr.*, 41, 4111 (1947); ibid., 23, 123 (1948); *Chem. Abstr.*, 44, 6395 (1950).
24. A. J. Fatiadi, *Synthesis*, 165 (1978).

Although an overall synthesis of 1,4-bis(dicyanomethylene)cyclohexane from hydroquinone has not been proposed or conducted previously, it is possible to construct such a synthesis by using methods from the above literature for each of the three individual steps. Choosing three of the best procedures for which experimental details are available (Refs. 18, 21, 4), this synthesis would afford the desired compound in ca. 85% overall yield from hydroquinone. But, this synthesis, reconstructed from the art-disclosed reactions, would require the use of three different solvents (alcohol, acetone, and water) with consequent need for isolation of intermediates at each stage.

In contrast, the entire synthesis scheme of the present invention involves three chemical reaction steps with combined reaction times totalling approximately one hour. The only other processing steps are two catalyst filtrations and the filtration of the final product. No organic solvents or solvent extraction steps are used at any point. The preferred Raney nickel and ruthenium oxide catalysts that are recovered can be reprocessed and used again.

DISCLOSURE OF INVENTION

The present invention encompasses a process for the preparation of 1,4-bis(dicyanomethylene)cyclohexane, comprising the steps:

I. hydrogenating hydroquinone to provide 1,4-cyclohexanediol;

II. oxidizing the 1,4-cyclohexanediol from Step (I) to provide 1,4-cyclohexanedione; and III. condensing the 1,4-cyclohexanedione from Step (II) with two equivalents of malononitrile.

The reaction can be carried out in a single portion of water (solvent), and without isolation of intermediate compounds.

The 1,4-bis(dicyanomethylene)cyclohexane which precipitates in Step (III) of the above process can be collected, e.g., by filtration, and dehydrogenated by any of several known methods (e.g., $MnO_2$/toluene or $Br_2$/pyridine) to provide high purity TCNQ.

BEST MODE OF CARRYING OUT THE INVENTION

The most preferred process herein is as follows:

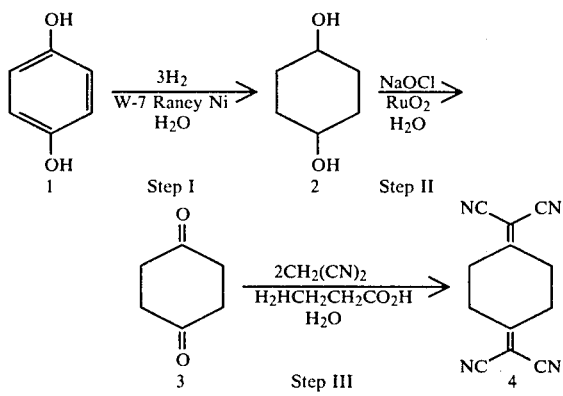

A brief overall description of the preferred process is as follows. Hydroquinone is dissolved in water to give a 20% solution. W-7 Raney nickel is added, and the resulting mixture is agitated under a hydrogen atmosphere. This reaction requires approximately 15–30 minutes at a temperature of 70°–80° C. and a hydrogen pressure of ca. 35 atmospheres. The Raney nickel is removed by filtration; to the resulting aqueous solution of 2 is added a catalytic quantity of ruthenium dioxide and a stoichiometric quantity of sodium hypochlorite solution. The hypochlorite addition requires approximately 30 minutes after which the ruthenium oxide catalyst is removed by filtration. To the resulting aqueous solution of 3 are added two equivalents of malononitrile and a catalytic quantity of beta-alanine. After neutralization of pH and brief warming and stirring the product 4 precipitates as a crystalline solid. It is collected by filtration, washed and dried, and is obtained in 92% yield based on hydroquinone. The product is obtained in suitable purity for conversion to TCNQ.

The following describes the preferred process in detail.

EXAMPLE I

Preparation of 1,4-Bis(dicyanomethylene)cyclohexane from Hydroquinone

Step I

A mixture of 88.1 g (0.80 mole) hydroquinone, 400 ml water, W-7 Raney nickel (prepared from 25 g Raney nickel/aluminum alloy in the manner of Ref. 6)* and 16 drops of 50% sodium hydroxide solution was placed in a 3.1 open glass liner and hydrogenated at 75° C. in a rocking autoclave. The initial hydrogen pressure was 500 psi, and complete hydrogen uptake required approximately 30 min. The catalyst was removed by filtration and washed with water.

*The procedure of Ref. 6 was modified in that the washings with alcohol were eliminated. The catalyst was washed with water and then used directly.

Step II

The combined filtrate and washings were placed in a 3 l. 3-neck flask fitted with a mechanical stirrer, thermometer, and addition funnel. A solution of 0.80 g ruthenium trichloride in 80 ml water was added. The resulting mixture was stirred, and 875 ml 2.07 M sodium hypochlorite solution was added dropwise over a period of 45 min. The solution temperature was maintained between 30° C. and 40° C. during the hypochlorite addition. Methanol (15 ml) was then added, after which the catalyst was removed by filtration and washed with water.

Step III

The combined filtrate and washings were placed in a 5 l. 3-neck flask fitted with a mechanical stirrer and thermometer. Malononitrile (128 g, 1.94 moles), beta-alanine (0.08 g) and 40 ml of saturated sodium bicarbonate solution were added. The solution was stirred, and the product began to precipitate almost immediately. The mixture was warmed briefly to 50° C., and then was cooled in ice. The product was collected by filtration, washed thoroughly with water and ether, and vacuum dried. 1,4-Bis(dicyanomethylene)cyclohexane was obtained as 152.7 g (92% yield based on hydroquinone) of pale beige powder, m.p. (corrected) 204°–210° C.

INDUSTRIAL APPLICABILITY

The process of the present invention involves three steps: I. Hydrogenation of hydroquinone (1) to the cyclohexanediol (2); II. oxidation of (2) to the cyclohexane diketone (3); and III. condensation of (3) with malononitrile.

In Step I of the process (hydrogenation), a wide range of temperatures (e.g., 20° C.–200° C.) and hydrogen pressures (e.g., 1–400 atm.) can be used. The reaction is generally carried out at a neutral-to-basic pH in the range of about 7–12. Considerable variation in type of equipment, method of agitation, and catalyst quantity can be tolerated. Hydrogenation catalysts other than the preferred W-7 Raney Ni can be used (e.g. rhodium on alumina; see Ref. 19).

In Step II (oxidation) various hypochlorite concentrations, other hypochlorite salts, and catalyst concentrations can be used. Other heavy metal oxides can be used in place of ruthenium oxide (see Ref. 20), but this is not preferred. $RuO_2$ (or its equivalent, i.e., various ruthenium salts that convert to the oxide in aqueous solution, e.g., $RuCl_3$) is highly preferred. Oxidation Step II can be carried out over a rather wide temperature range, preferably from about 20° C. to about 90° C.

The only significant variable in Step III (condensation) is the catalyst. Beta-alanine is preferred, but a wide variety of catalysts are known in the literature to effect this type of condensation (see Ref. 24, p. 178). This condensation occurs rapidly at a temperature in the range of 25° C. to 100° C., but other temperatures can be used.

The published method for the synthesis of 4 from 3 as an isolated synthetic step also uses water as a solvent and beta-alanine as catalyst, and achieves 97% yield (Ref. 4). The conditions used here in Step III are essentially the same as this. However, the method used in Ref. 4 to obtain 1,4-cyclohexanedione is self-condensation of diethyl succinate followed by decarboxyethylation (Ref. 5); this is a difficult and inconvenient procedure, and affords 3 in a maximum yield of only 61%. Thus, the overall yield of 4 obtained in the original published procedures (Ref. 4) is only 59%.

An essential feature of the present invention resides in the choice of a method for preparing 3 as an aqueous solution, starting from a readily available chemical (hydroquinone), and employing reactions that use only water as solvent (Steps I and II). It is this unique combination of reactions that allows all three steps to be run in a single quantity of water. The intrinsically high yields of these reactions are maintained because isolation/purification of intermediates is unnecessary.

The W-7 Raney nickel catalyst was chosen in Step I to allow this reaction to be run under conditions that are exceptionally mild for hydrogenation of an aromatic ring. The combination of hydroquinone with W-7 Raney nickel is reported in Ref. 6. Other forms of Raney nickel are not effective with hydroquinone, and other polyhydric phenols are not reduced readily with the W-7 catalyst. In the published work on this reaction, ethanol was used as solvent. But, the use of water as solvent for W-7 Raney nickel hydrogenation of hydroquinone is especially important for an industrial scale synthesis. Also, W-7 Raney nickel is the simplest of the "W" catalysts to prepare, and its use in water makes catalyst preparation even easier. Hydroquinone has been hydrogenated with a variety of other catalysts under high temperature and/or high pressure conditions (Refs. 7–19).

The hypochlorite/ruthenium oxide oxidation method is used in Step II because this is one of the few alcohol oxidation techniques that uses water as solvent. Most alcohol oxidations require an organic solvent, so that this is a rare and little-used method. It is uniquely suited to the present process because both 2 and 3 are highly soluble in water. The hypochlorite oxidation has been used to oxidize cyclohexanol to cyclohexanone (Ref. 20), but has not previously been applied to the oxidation of 2.

Various other methods have been used to oxidize 2 to 3 (refs. 10, 21–23). The best is probably Jones oxidation which affords 91% yield (Ref. 21), but which used acetone as the reaction solvent.

The 1,4-Bis(dicyanomethylene)cyclohexane prepared in the manner of this invention can be hydrogenated to TCNQ by well-known methods (Refs. 3 and 4) for use in a variety of industrial applications (Refs. 3 and 3 and U.S. Pat. No. 4,148,811).

EXAMPLE II

Preparation of TCNQ from 1,4-Bis(dicyanomethylene) cyclohexane 1,4-Bis(dicyanomethylene)cyclohexane prepared in the manner of Example I, above, can be dehydrogenated by a variety of means to provide TCNQ. The following exemplifies two excellent means for effecting dehydrogenation.

Method 1

According to the procedure of Acker, et al., cited as Reference 4, above, the 1,4-bis(dicyanomethylene)cyclohexane is allowed to react with N-bromosuccinimide in acetonitrile to provide TCNQ in ca. 84% yields. Several other excellent methods for securing TCNQ from 1,4-bis(dicyanomethylene)cyclohexane appear in this reference.

Method 2

According to the procedure of Fatiadi Synthesis, 1976, 133, incorporated herein by reference, the 1,4-bis(dicyanomethylene)cyclohexane is allowed to react with manganese dioxide in refluxing (110° C.) toluene for ca. 15 minutes to provide TCNQ in ca. 60% yields.

What is claimed is:

1. A process for the preparation of 1,4-bis(dicyanomethylene)cyclohexane, comprising the steps:
   I. hydrogenating hydroquinone to provide 1,4-cyclohexanediol;
   II. oxidizing the 1,4-cyclohexanediol from Step (I) in the presence of a ruthenium catalyst to provide 1,4-cyclohexanedione; and
   III. condensing the 1,4-cyclohexanedione from Step (II) with two equivalents of malononitrile said steps (I), (II) and (III) each being carried out in water as the reaction solvent.

2. A process according to claim 1 wherein hydrogenation Step (I) is carried out using W-7 Raney nickel.

3. A process according to claim 1 wherein oxidation step (II) is carried out using a ruthenium oxide or its equivalent, catalyst.

4. A process according to claim 3 wherein the ruthenium catalyst is ruthenium oxide, or its equivalent, and the oxidizing agent is hypochlorite.

5. A process according to claim 1 wherein condensation Step (III) is carried out in the presence of beta-alanine as the catalyst.

6. A process according to claim 1, comprising: hydrogenating hydroquinone in the presence of W-7 Raney nickel catalyst and water solvent to provide 1,4-cyclohexanediol; (II) oxidizing the 1,4-cyclohexanediol from Step (I) with sodium hypochlorite in the presence of a ruthenium oxide catalyst, or its equivalent, in water solvent to provide 1,4-cyclohexanedione; and (III) condensing the 1,4-cyclohexanedione from Step (II) with two equivalents of malononitrile in the presence of beta-alanine catalyst in water solvent, whereupon 1,4-bis(dicyanomethylene(cyclohexane precipitates from said water solvent.

* * * * *